United States Patent
Ishii et al.

(10) Patent No.: US 10,508,191 B2
(45) Date of Patent: Dec. 17, 2019

(54) FLAME-RETARDANT POLYCARBONATE RESIN COMPOSITION, SHEET AND FILM EACH USING SAME, AND METHOD FOR PRODUCING SAID SHEET OR FILM

(71) Applicants: MITSUBISHI GAS CHEMICAL COMPANY, INC., Tokyo (JP); MGC FILSHEET CO., LTD., Saitama (JP)

(72) Inventors: Hiroki Ishii, Fukushima (JP); Haruhiko Kurokawa, Kanagawa (JP); Atsuhiro Tokita, Osaka (JP)

(73) Assignees: MITSUBUSHI GAS CHEMICAL COMPANY, INC., Tokyo (JP); MGC FILSHEET CO., LTD., Saitama (JP)

( * ) Notice: Subject to any disclaimer, the term of this patent is extended or adjusted under 35 U.S.C. 154(b) by 0 days.

(21) Appl. No.: 15/743,884

(22) PCT Filed: Aug. 29, 2016

(86) PCT No.: PCT/JP2016/075133
§ 371 (c)(1),
(2) Date: Jan. 11, 2018

(87) PCT Pub. No.: WO2017/038736
PCT Pub. Date: Mar. 9, 2017

(65) Prior Publication Data
US 2018/0201754 A1   Jul. 19, 2018

(30) Foreign Application Priority Data

Aug. 31, 2015 (JP) .................................. 2015-171096

(51) Int. Cl.
| | |
|---|---|
| C08K 5/00 | (2006.01) |
| C08L 69/00 | (2006.01) |
| C08K 5/521 | (2006.01) |
| C08K 5/5399 | (2006.01) |
| C08K 7/20 | (2006.01) |
| C08L 27/12 | (2006.01) |
| G01N 25/48 | (2006.01) |

(52) U.S. Cl.
CPC ............ *C08K 5/0066* (2013.01); *C08K 5/521* (2013.01); *C08K 5/5399* (2013.01); *C08K 7/20* (2013.01); *C08L 69/00* (2013.01); *C08F 2500/02* (2013.01); *C08F 2500/12* (2013.01); *C08L 27/12* (2013.01); *G01N 25/4866* (2013.01)

(58) Field of Classification Search
CPC ..................................................... C08K 5/5399
See application file for complete search history.

(56) References Cited

U.S. PATENT DOCUMENTS

2015/0025180 A1   1/2015  Monden

FOREIGN PATENT DOCUMENTS

| JP | 2006-316149 A | 11/2006 |
|---|---|---|
| JP | 2008-222813 A | 9/2008 |
| JP | 2010-70590 A | 4/2010 |
| JP | 2013-64047 A | 4/2013 |
| JP | 2013-194200 A | 9/2013 |
| JP | 2013-224349 A | 10/2013 |
| WO | 2013/115151 A1 | 8/2013 |

OTHER PUBLICATIONS

English machine translation of Yokoyama, JP 2013-064047A (Year: 2013).*
International Search report from Patent Application No. PCT/JP2016/075133, dated Sep. 20, 2016.

* cited by examiner

*Primary Examiner* — Peter F Godenschwager
(74) *Attorney, Agent, or Firm* — Greenblum & Bernstein, P.L.C.

(57) ABSTRACT

The present invention provides: a polycarbonate resin composition which contains 18-75% by mass of (A) a polycarbonate resin having a viscosity average molecular weight of 28,000-60,000, 5-30% by mass of (B) a phosphorus flame retardant, 18-50% by mass of (C) a fibrous or plate-like inorganic filler, and 0.1-2% by mass of (D) a fluoropolymer; and a sheet and a film, each of which uses this polycarbonate resin composition.

10 Claims, No Drawings

FLAME-RETARDANT POLYCARBONATE RESIN COMPOSITION, SHEET AND FILM EACH USING SAME, AND METHOD FOR PRODUCING SAID SHEET OR FILM

TECHNICAL FIELD

The present invention relates to a flame-retardant polycarbonate resin composition reinforced with an inorganic filler, a sheet or film using the same, and a method for the production thereof.

BACKGROUND ART

Polycarbonate resins are excellent in transparency, impact resistance, heat resistance and the like, and in addition, molded products obtained therefrom are excellent in size stability and the like. For this reason, polycarbonate resins are widely used as raw material resins for the production of housings of electrical and electronic equipments, automobile parts, and precision molded products such as parts related to optical disks. In particular, as cases of home appliances, electronic equipments and image display devices, etc., products having high commercial value can be obtained, taking advantage of beautiful outer appearance thereof. Further, reinforced polycarbonate resins, in which various inorganic fillers are added to polycarbonate resins, are also used for a wide range of purposes because of excellent mechanical strength and heat resistance thereof.

Recently, reduction in size and thickness of electronic equipments including information/mobile devices as described above has been accelerated. For this reason, as a material to be used, a sheet/film having excellent mechanical properties and good flame retardance even in the case where the thickness thereof is reduced has been desired.

In particular, the size and thickness of cases of electrical and electronic equipments, etc. have been extremely reduced because of tendency of reduction in size of such equipments themselves. For this reason, high flame retardance, for example, V-1 or higher in the UL94 vertical burning test even in the case where the thickness is 0.8 mm or less, has been desired.

When preparing such a thin-walled molded product, an extrusion molding machine including sheet/film molding is more advantageous than an injection molding machine. In particular, when an inorganic filler is contained for the improvement of mechanical properties, since the flowability of a resin composition is reduced, it is difficult to perform large-area molding with a thickness of 0.8 mm or less by means of injection molding. Further, when employing a multiple gate for large-area molding, problems such as reduction in properties and poor outer appearance are caused by a weld. Meanwhile, extrusion-molded products do not have these problems because the range of the flowability appropriate for molding is different from that of injection-molded products, and therefore it is possible to perform large-area molding continuously.

Patent Document 1 describes a polycarbonate resin composition, wherein a glass fiber is used as an inorganic filler and a metal salt-based flame retardant or organic phosphorus-based flame retardant is used as a flame retardant. Patent Document 1 describes that the viscosity average molecular weight of polycarbonate resin is particularly preferably 14,000 to 24,000, and in the Examples, the viscosity average molecular weight is 22,400, and flame retardance is V-0 in the case where the thickness is 0.8 mm or 1.6 mm. Patent Document 2 describes a polycarbonate resin composition, wherein a glass fiber is used as an inorganic filler and a phosphazene compound is used as a flame retardant. Patent Document 2 describes that the viscosity average molecular weight of polycarbonate resin is particularly preferably 17,000 to 24,000, and in the Examples, the viscosity average molecular weight is 21,000, and flame retardance is V-0 in the case where the thickness is 1.0 mm.

However, in the case of the compositions described in Patent Documents 1 and 2, flame retardance is insufficient when a molded product has a smaller thickness. Moreover, since these are flame-retardant polycarbonate resin compositions to be used for injection molding, it is difficult to obtain a thin-walled film/sheet having a large area.

Patent Document 3 describes a polycarbonate resin composition for extrusion molding. Patent Document 3 describes that the viscosity-average molecular weight is particularly preferably 17,000 to 28,000, and in the Examples, flame retardance is V-0 in the case where the thickness is 0.5 mm.

However, since the composition described in Patent Document 3 does not contain an inorganic filler, sufficient bending characteristics cannot be obtained, and mechanical strength is insufficient.

PRIOR ART DOCUMENTS

Patent Documents

Patent Document 1: Japanese Laid-Open Patent Publication No. 2010-70590
Patent Document 2: Japanese Laid-Open Patent Publication No. 2013-224349
Patent Document 3: Japanese Laid-Open Patent Publication No. 2008-222813

SUMMARY OF THE INVENTION

Problems to be Solved by the Invention

When using the polycarbonate resin compositions described in Patent Documents 1-3, it was impossible to obtain a sheet/film having all of excellent heat resistance, excellent mechanical strength (particularly rigidity) and excellent flame retardance.

The purpose of the present invention is to provide: a polycarbonate resin composition, which is suitable for a sheet or film made of a polycarbonate resin having excellent heat resistance, excellent mechanical strength (particularly rigidity), and excellent flame retardance even in the case where the sheet or film is thin; and a sheet or film obtained by using the same.

Means for Solving the Problems

The present inventors diligently made researches in order to solve the above-described problems, and found that the problems can be solved by using a polycarbonate resin composition, which contains a polycarbonate resin having a viscosity average molecular weight of 28,000 to 60,000, a phosphorus-based flame retardant, a fibrous or plate-like inorganic filler and a fluoropolymer.

Specifically, the present invention is as described below.
[1] A polycarbonate resin composition, which contains 18 to 75% by mass of a polycarbonate resin (A) having a viscosity average molecular weight of 28,000 to 60,000, 5 to 30% by mass of a phosphorus-based flame retardant (B), 18 to 50% by mass of a fibrous or plate-like inorganic filler (C) and 0.1 to 2% by mass of a fluoropolymer (D).

[2] The polycarbonate resin composition according to item [1], which has a melt volume rate of 2.0 to 10 cm$^3$/10 min under 300° C. and 1.2 kg.
[3] The polycarbonate resin composition according to item [1] or [2], wherein the phosphorus-based flame retardant (B) is a phosphazene compound or a condensed-type phosphoric acid ester.
[4] The polycarbonate resin composition according to any one of items [1] to [3], wherein the phosphorus-based flame retardant (B) is a phosphazene compound.
[5] The polycarbonate resin composition according to any one of items [1] to [4], wherein the content of the inorganic filler (C) is 22.5 to 50% by mass.
[6] The polycarbonate resin composition according to any one of items [1] to [5], wherein the inorganic filler (C) is a glass fiber.
[7] The polycarbonate resin composition according to any one of items [1] to [6], which is for a sheet or film.
[8] A sheet or film, wherein the polycarbonate resin composition according to any one of items [1] to [7] is used.
[9] The sheet or film according to item [8], which has a thickness of 400 to 1200 μm.
[10] The sheet or film according to item [8] or [9], wherein the evaluation result of the UL94V test is V-0 or V-1.
[11] The sheet or film according to any one of items [8] to [10], wherein a resin component containing the polycarbonate resin (A), the phosphorus-based flame retardant (B) and the fluoropolymer (D) has a glass transition temperature of 75° C. or higher.
[12] A method for producing a sheet or film, which comprises extrusion molding the polycarbonate resin composition according to any one of items [1] to [7].

Advantageous Effect of the Invention

According to the present invention, it is possible to obtain a sheet or film made of a polycarbonate resin, which has excellent heat resistance, excellent mechanical strength (particularly rigidity), and excellent flame retardance even in the case where the sheet or film is thin.

BEST MODE FOR CARRYING OUT THE INVENTION

Hereinafter, the present invention will be described in detail. Note that the present invention is not limited to the below-described embodiments, and can be arbitrarily changed and then carried out without departing from the gist of the present invention. Note that all the documents and publications cited herein are incorporated herein by reference in their entireties regardless of purposes thereof. In addition, the contents disclosed in the claims, specification, drawings and abstract of Japanese Patent Application No. 2015-171096 (filed on Aug. 31, 2015), to which priority is claimed by the present application, are incorporated herein by reference in their entireties.

One embodiment of the present invention is a polycarbonate resin composition, which contains 18 to 75% by mass of a polycarbonate resin (A) having a viscosity average molecular weight of 28,000 to 60,000, 5 to 30% by mass of a phosphorus-based flame retardant (B), 18 to 50% by mass of a fibrous or plate-like inorganic filler (C) and 0.1 to 2% by mass of a fluoropolymer (D). When using the polycarbonate resin composition of this embodiment, it is possible to obtain a sheet or film made of a polycarbonate resin, which has excellent heat resistance, excellent mechanical strength (particularly rigidity), and excellent flame retardance even in the case where the sheet or film is thin.

Conventionally, an inorganic filler such as a glass fiber and a phosphorus-based flame retardant are generally used in a resin composition for improving mechanical properties and for imparting flame retardance, respectively. However, in the case of a polycarbonate resin composition in which both the materials are used in combination, dripping occurs more easily in the UL94 vertical burning test when a molded product is thinner, and sufficient flame retardance cannot be obtained. The present inventors diligently made researches in order to solve the problem, and found that dripping occurs more easily at the time of burning when a molded product is thinner and flame retardance is reduced because the specific gravity of a composition is increased by blending of a flame retardant such as a glass fiber and because the heat resistance and viscosity of the resin composition are reduced by blending of the flame retardant. Further, the present inventors found that a sheet or film made of a polycarbonate resin, which has excellent heat resistance, excellent mechanical strength (particularly rigidity), and excellent flame retardance even in the case where the sheet or film is thin, can be obtained by adjusting the type and blending ratio of each component constituting a polycarbonate resin composition, in particular, the type and blending ratio of the inorganic filler (C), and by adjusting the viscosity average molecular weight of the polycarbonate resin (A).

Hereinafter, constituents of the polycarbonate resin composition of the present invention will be described.

[Polycarbonate Resin (A)]

The type of the polycarbonate resin (A) (hereinafter sometimes referred to as "the component (A)") to be used in the present invention is not particularly limited, but an aromatic polycarbonate resin is particularly preferably used in terms of heat resistance, mechanical properties and electrical characteristics. The polycarbonate resin is a branched or unbranched thermoplastic polymer or copolymer, which is obtained by reacting a dihydroxy compound or this and a small amount of a branching agent with phosgene or triphosgene or carbonic acid diester.

The method for producing the polycarbonate resin is not particularly limited, and it is possible to use a polycarbonate resin produced by a conventionally known phosgene method (interfacial polymerization method), melting method (transesterification method) or the like. Further, in the case of using the melting method, it is possible to use a polycarbonate resin in which the amount of OH groups of terminal groups is adjusted.

Examples of the dihydroxy compound as a raw material include 2,2-bis(4-hydroxyphenyl)propane (i.e., "bisphenol A"), tetramethylbisphenol A, bis(4-hydroxyphenyl)-p-diisopropylbenzene, hydroquinone, resorcinol and 4,4-dihydroxydiphenyl. Two or more of these compounds may be used in combination. In terms of impact resistance and heat resistance, it is preferred to use bisphenol A as the main component. The polycarbonate resin containing bisphenol A as the main component is a polycarbonate resin, wherein the ratio of bisphenol A in bisphenols used is 60 to 100 mol %, and preferably 90 to 100 mol %. Further, it is also possible to use a compound in which at least one tetraalkylphosphonium sulfonate is bound to the above-described aromatic dihydroxy compound.

Further, the polycarbonate resin may be a copolymer mainly composed of a polycarbonate resin such as a copolymer of the dihydroxy compound and a compound having a siloxane structure.

For obtaining a branched polycarbonate resin, a part of the above-described dihydroxy compound may be substituted with a branching agent. The branching agent is not particularly limited, and examples thereof include a polyhydroxy compound such as phloroglucin, 4,6-dimethyl-2,4,6-tri(4-hydroxyphenyl)heptene-2, 4,6-dimethyl-2,4,6-tri(4-hydroxyphenyl)heptane, 2,6-dimethyl-2,4,6-tri(4-hydroxyphenyl)heptene-3, 1,3,5-tri(4-hydroxyphenyl)benzene and 1,1,1-tri(4-hydroxyphenyl)ethane, and 3,3-bis(4-hydroxyaryl)oxyindole (i.e., "isatinbisphenol"), 5-chloroisatin, 5,7-dichloroisatin and 5-bromoisatin. The amount of the compound to be used for substitution is usually 0.01 to 10 mol %, and preferably 0.1 to 2 mol % relative to the dihydroxy compound.

As the polycarbonate resin (A), among the above-described ones, preferred is a polycarbonate resin derived from 2,2-bis(4-hydroxyphenyl)propane (i.e., "bisphenol A") or a polycarbonate copolymer derived from 2,2-bis(4-hydroxyphenyl)propane (i.e., "bisphenol A") and another aromatic dihydroxy compound.

The above-described polycarbonate resins may be used solely, or two or more of them may be used by mixing thereof.

For adjusting the molecular weight of the polycarbonate resin (A), as a terminating agent, a monovalent hydroxy compound, for example, an aromatic hydroxy compound may be used. Examples of the monovalent aromatic hydroxy compound include m- and p-methylphenol, m- and p-propylphenol, p-tert-butylphenol and p-long chain alkyl substituted phenol.

Regarding the molecular weight of the polycarbonate resin (A) to be used in the present invention, the viscosity average molecular weight [Mv] is 28,000 to 60,000 in consideration of moldability, strength of molded products, etc. When the viscosity average molecular weight of the polycarbonate resin (A) is 28,000 or more, the resin composition has high viscosity, and it is possible to prevent dripping during the burning test, in particular, dripping during the burning test in the case of a thin film because deformation during melting is suppressed, and therefore it is preferred in terms of flame retardance. Meanwhile, when the viscosity average molecular weight of the polycarbonate resin (A) is 60,000 or less, increase of screw torque at the time of melt extrusion can be suppressed, and it is more preferred in terms of easiness of molding. The viscosity average molecular weight is preferably 30,000 to 55,000, and more preferably 35,000 to 50,000 in terms of the effect of preventing dripping during the burning test and easiness of molding.

In this regard, the viscosity-average molecular weight [Mv] of the polycarbonate resin can be measured by the below-described method.

<Measurement Conditions for Viscosity-Average Molecular Weight (Mv)>

As a solvent, methylene chloride is used, the limiting viscosity [η] (unit: dl/g) at 20° C. is obtained using an Ubbelohde viscometer, and calculation is made according to Schnell's viscosity equation described below, thereby obtaining a value of the viscosity-average molecular weight [Mv].

$\eta = 1.23 \times 10^{-4} \times Mv^{0.83}$  <Schnell's viscosity equation>

In this regard, the value of the limiting viscosity [η] is obtained by carrying out the measurement of the specific viscosity [$\eta_{sp}$] with each solution concentration [C] (g/dl) and calculation according to the below-described formula.

$$\eta = \lim_{c \to 0} \eta_{sp}/c$$

[Phosphorus-Based Flame Retardant (B)]

The polycarbonate resin composition of the present invention contains the phosphorus-based flame retardant (B) for the improvement of flame retardance.

As the phosphorus-based flame retardant (B), a phosphoric acid ester-based flame retardant, a phosphazene-based flame retardant, etc., can be used. As the phosphorus-based flame retardant (B), such flame retardants may be used solely, or two or more of them may be used as a mixture.

<Phosphoric Acid Ester-Based Flame Retardant>

In particular, a phosphoric acid ester-based flame retardant is preferably used because it has high flame retardant effect and also has flowability improvement effect. The phosphoric acid ester-based flame retardant is not limited, but it is particularly preferably a phosphoric acid ester-based compound represented by general formula (IIa) below.

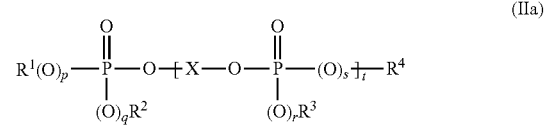

(In formula (IIa): $R^2$, $R^3$ and $R^4$ each independently represent a $C_{1-8}$ alkyl group which may be substituted with a $C_{1-8}$ alkoxy group, or a $C_{6-20}$ aryl group which may be substituted with a $C_{1-8}$ alkyl group or phenyl which may be substituted with a $C_{1-8}$ alkyl group; p, q, r and s are each independently 0 or 1; t is an integer of 0 to 5; and X represents an arylene group or a divalent group represented by formula (IIb) below.)

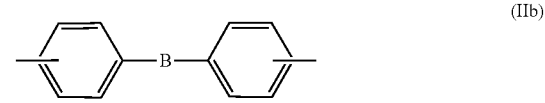

(In formula (IIb): B is a single bond, —C(CH$_3$)$_2$—, —SO$_2$—, —S— or —O—.)

In the above-described general formula (IIa), examples of the aryl group of $R^1$ to $R^4$ include a phenyl group and a naphthyl group. Further, examples of the arylene group of X include a phenylene group and a naphtylene group. When t is 0, the compound represented by general formula (IIa) is a phosphoric acid ester, and when t is larger than 0, the compound is a condensed phosphoric acid ester (including a mixture). In the present invention, the condensed phosphoric acid ester is particularly preferably used.

Specific examples of the phosphoric acid ester-based flame retardant represented by general formula (IIa) above include trimethyl phosphate, triethyl phosphate, tributyl phosphate, trioctyl phosphate, tributoxyethyl phosphate, triphenyl phosphate, tricresyl phosphate, tricresylphenyl phosphate, octyldiphenyl phosphate, diisopropylphenyl phosphate, bisphenol A tetraphenyl diphosphate, bisphenol A tetracresyl diphosphate, bisphenol A tetraxylyl diphosphate, hydroquinone tetraphenyl diphosphate, hydroquinone tetracresyl diphosphate, hydroquinone tetraxylyl diphosphate, resorcinol tetraphenyl diphosphate, resorcinol bisdixylenyl phosphate, etc. Among them, preferred are triphenyl phosphate, bisphenol A tetraphenyl diphosphate, resorcinol tetraphenyl diphosphate, resorcinol bisdi-2,6-xylenyl phosphate, etc. Examples of commercially-available phosphoric acid ester-based flame retardants include FP-600 manufactured by ADEKA Corporation and PX-200 manufactured by Daihachi Chemical Industry Co., Ltd.

The above-described phosphoric acid ester-based flame retardants may be used solely, or two or more of them may be used as a mixture.

<Phosphazene-Based Flame Retardant>

The phosphazene-based flame retardant can suppress reduction in heat resistance of the resin composition due to addition of the flame retardant more than the phosphoric acid ester-based flame retardant, and therefore can be used as an effective phosphorus-based flame retardant. The phosphazene-based flame retardant is an organic compound having a —P=N— bond in the molecule. Preferred examples of the phosphazene-based flame retardant include a cyclic phosphazene compound represented by general formula (IIIa) below, a linear phosphazene compound represented by general formula (IIIb) below, and a crosslinked phosphazene compound in which at least one phosphazene compound selected from the group consisting of compounds of general formulae (IIIa) and (IIIb) below is crosslinked with a crosslinking group. As the crosslinked phosphazene compound, those obtained by crosslinking with a crosslinking group represented by general formula (IIIc) below are preferred in terms of flame retardance.

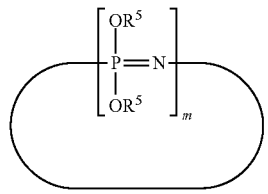
(IIIa)

(In formula (IIIa): m is an integer of 3 to 25; and $R^5$s may be the same or different and represent an aryl group or an alkylaryl group.)

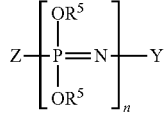
(IIIb)

(In formula (IIIb): n is an integer of 3 to 10,000; Z represents a —N=P(OR$^5$)$_3$ group or a —N=P(O)OR$^5$ group; and Y represents a —P(OR$^5$)$_4$ group or a —P(O)(OR$^5$)$_2$ group. $R^5$s may be the same or different and represent an aryl group or an alkylaryl group.)

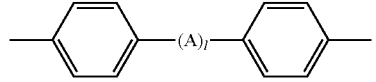
(IIIc)

(In formula (IIIc): A is —C(CH$_3$)$_2$—, —SO$_2$—, —S— or —O—; and l is 0 or 1.)

Preferred examples of cyclic and/or linear phosphazene compounds represented by general formulae (IIIa) and (IIIb) include those in which $R^5$ is a $C_{6-20}$ aryl group which may be substituted with a $C_{1-6}$ alkyl group. Specific examples thereof include: a cyclic or linear phosphazene compound in which $R^5$ is an aryl group such as a phenyl group; a cyclic or linear phenoxyphosphazene in which $R^5$ is a $C_{6-20}$ aryl group which is substituted with a $C_{1-6}$, preferably $C_{1-3}$ alkyl such as a tolyl group (o-, m- or p-tolyloxy group) and a xylyl group (2,3-, 2,6- or 3,5-xylyl group); and a cyclic or linear phenoxyphosphazene in which the above-described $R^5$s are combined. More specific examples thereof include: a cyclic and/or linear $C_{1-6}$ alkyl $C_{6-20}$ aryloxy phosphazene such as phenoxyphosphazene, (poly)tolyloxyphosphazene (e.g., o-tolyloxyphosphazene, m-tolyloxyphosphazene, p-tolyloxyphosphazene, o,m-tolyloxyphosphazene, o,p-tolyloxyphosphazene, m,p-tolyloxyphosphazene, o,m,p-tolyloxyphosphazene, etc.) and (poly)xylyloxyphosphazene; and a cyclic and/or linear $C_{6-20}$ aryl $C_{1-10}$ alkyl $C_{6-20}$ aryloxy phosphazene such as (poly)phenoxytolyloxyphosphazene (e.g., phenoxy-o-tolyloxyphosphazene, phenoxy-m-tolyloxyphosphazene, phenoxy-p-tolyloxyphosphazene, phenoxy-o,m-tolyloxyphosphazene, phenoxy-o,p-tolyloxyphosphazene, phenoxy-m,p-tolyloxyphosphazene, phenoxy-o,m,p-tolyloxyphosphazene, etc.), (poly)phenoxyxylyloxyphosphazene and (poly)phenoxytolyloxyxylyloxyphosphazene. Preferred are a cyclic and/or linear phenoxyphosphazene, a cyclic and/or linear $C_{1-3}$ alkyl $C_{6-20}$ aryloxy phosphazene, and a $C_{6-20}$ aryloxy $C_{1-3}$ alkyl $C_{6-20}$ aryloxy phosphazene (e.g., a cyclic and/or linear tolyloxyphosphazene, a cyclic and/or linear phenoxytolylphenoxyphosphazene, etc.). In this regard, "$C_{1-6}$" means that "the carbon number is 1 to 6", and the same applies to "$C_{6-20}$", "$C_{1-10}$", etc. Further, "(poly)phenoxy . . . " means one or both of "phenoxy . . . " and "polyphenoxy . . . ".

As the cyclic phosphazene compound represented by general formula (IIIa), a cyclic phenoxyphosphazene in which $R^5$ is a phenyl group is particularly preferred. Further, the cyclic phenoxyphosphazene compound is preferably a compound represented by general formula (IIIc), wherein m is an integer of 3 to 8, and may also be a mixture of compounds in which the numbers for m differ from each other. Specific examples thereof include compounds such as hexaphenoxycyclotriphosphazene (compound in which m is 3), octaphenoxycyclotetraphosphazene (compound in which m is 4) and decaphenoxycyclopentaphosphazene (compound in which m is 5), and mixtures thereof. Among them, preferred is a mixture containing 50% by mass or more of a compound in which m is 3, 10 to 40% by mass of a compound in which m is 4 and 30% by mass or less of compounds in which m is 5 or more.

For example, ammonium chloride is reacted with phosphorus pentachloride at 120 to 130° C. to obtain a mixture of cyclic and linear chlorophosphazenes, from which cyclic chlorophosphazenes such as hexachlorocyclotriphosphazene, octachlorocyclotetraphosphazene and decachlorocyclopentaphosphazene are taken out, and then these are subjected to substitution with a phenoxy group, thereby obtaining the above-described cyclic phenoxyphosphazene compound.

As the linear phosphazene compound represented by general formula (IIIb), a linear phenoxyphosphazene in which $R^5$ is a phenyl group is particularly preferred. Examples of the above-described linear phenoxyphosphazene compound include compounds obtained by subjecting a chloride of the cyclic phenoxyphosphazene compound obtained by the above-described method (e.g., hexachlorocyclotriphosphazene) to ring-opening polymerization at 220 to 250° C. and substituting a linear dichlorophosphazene having a polymerization degree of 3 to 10,000 obtained with a phenoxy group. Regarding the linear phenoxyphosphazene compound, n in general formula (IIIb) is preferably 3 to 1,000, more preferably 3 to 100, and even more preferably 3 to 25.

Examples of the crosslinked phenoxyphosphazene compound include compounds having a crosslinked structure of a 4,4'-diphenylene group such as a compound having a crosslinked structure of 4,4'-sulfonyldiphenylene (bisphenol S residue), a compound having a crosslinked structure of a 2,2-(4,4'-diphenylene)isopropylidene group, a compound having a crosslinked structure of a 4,4'-oxydiphenylene group, and a compound having a crosslinked structure of a 4,4'-thiodiphenylene group.

Further, as the crosslinked phosphazene compound, a crosslinked phenoxyphosphazene compound, wherein a cyclic phenoxyphosphazene compound in which $R^5$ in general formula (IIIa) is a phenyl group is crosslinked with a crosslinking group represented by general formula (IIIc) above, or a crosslinked phenoxyphosphazene compound, wherein a linear phenoxyphosphazene compound in which $R^5$ in general formula (IIIb) above is a phenyl group is crosslinked with a crosslinking group represented by general formula (IIIc) above, is preferred in terms of flame retardance, and a crosslinked phenoxyphosphazene compound, wherein the cyclic phenoxyphosphazene compound is crosslinked with a crosslinking group represented by general formula (IIIc) above, is more preferred.

Further, the content of the phenylene group in the crosslinked phosphazene compound is usually 50 to 99.9%, and preferably 70 to 90% based on the total number of the phenyl group and the phenylene group in the cyclic phosphazene compound represented by general formula (IIIa) and/or the linear phenoxyphosphazene compound represented by general formula (IIIb). Moreover, the crosslinked phenoxyphosphazene compound is particularly preferably a compound not having a free hydroxyl group in the molecule.

In the present invention, in terms of flame retardance and mechanical properties, the phosphazene-based flame retardant is preferably at least one selected from the group consisting of a cyclic phenoxyphosphazene compound represented by general formula (IIIa) above and a crosslinked phenoxyphosphazene compound, wherein a cyclic phenoxyphosphazene compound represented by general formula (IIIa) above is crosslinked with a crosslinking group. Examples of commercially-available phosphazene-based flame retardants include "Rabitle FP-110" and "Rabitle FP-110T" manufactured by Fushimi Pharmaceutical Co., Ltd. and "SPS100" manufactured by Otsuka Chemical Co., Ltd. which are cyclic phenoxyphosphazenes.

The above-described phosphazene-based flame retardants may be used solely, or two or more of them may be used as a mixture.

[Fibrous or Plate-Like Inorganic Filler (C)]

The polycarbonate resin composition of the present invention contains a fibrous or plate-like inorganic filler. Every inorganic filler is generally classified into a fibrous inorganic filler, a plate-like inorganic filler or a spherical inorganic filler (beads) based on its shape. The fibrous inorganic filler and the plate-like inorganic filler are excellent in effects of reinforcing resin compositions, in particular, rigidity including bending elastic modulus and bending strength of molded products, compared to the spherical inorganic filler.

As the fibrous or plate-like inorganic filler to be used in the present invention, at least one selected from a glass-based reinforcing material, a carbon-based reinforcing material and a silicate-based reinforcing material can be used because these materials are excellent in effects of reinforcing polycarbonate resin compositions, in particular, rigidity including bending elastic modulus and bending strength of molded products. Among them, a glass-based reinforcing material is particularly preferably used. As the fibrous or plate-like inorganic filler, such materials may be used solely, or two or more of them may be used as a mixture.

<Glass-Based Reinforcing Material>

The type of the glass-based reinforcing material is not particularly limited, and it is sufficient when the material has a fibrous shape or plate-like shape.

Examples of fibrous glass-based reinforcing materials, i.e., glass fibers include a chopped strand and a roving glass, and any publicly-known glass fiber in any form can be used, but from the viewpoint of productivity, a chopped strand (chopped glass fiber) is preferred. A glass fiber chopped strand is a product, wherein a glass fiber (strand) obtained by bundling several tens to several thousands of single glass fibers (filaments) is cut to have a predetermined length. Note that the glass fiber may be in any form at the time of blending the polycarbonate resin and the glass fiber (long fiber) in a masterbatch or the like. Specifically, a resin in which the glass fiber is kneaded at a high ratio (masterbatch) and a resin in which no glass fiber is kneaded are mixed and kneaded, thereby producing a resin composition in which a predetermined amount of the glass fiber is blended.

Examples of the plate-like glass-based reinforcing material include a glass flake. The glass flake is usually a scaly glass powder having an average particle diameter of 10 to 4000 μm, an average thicknesses of 0.1 to 10 μm and an aspect ratio (ratio of average maximum diameter/average thicknesses) of about 2 to 1000.

One type of a fibrous or plate-like glass-based reinforcing material may be used solely, or two or more types of fibrous or plate-like glass-based reinforcing materials may be used as a mixture. For example, two or more types of glass fibers (including a milled fiber) respectively having different average fiber diameters, average lengths and the like may be used in combination, and two or more types of glass flakes respectively having different average particle diameters, average thicknesses and aspect ratios may be used in combination. Further, one or more types of glass fibers (including a milled fiber) may be used in combination, and one or more types of flakes may be used in combination with one or more types of glass fibers (including a milled fiber).

For the purpose of size stabilization, particle glass beads may be used in combination.

<Carbon-Based Reinforcing Material>

Examples of the carbon-based reinforcing material include a carbon fiber, a carbon nanotube, etc. as a fibrous filler, and graphite as a plate-like filler. Among them, a carbon fiber and graphite are preferably used.

One type of a carbon-based reinforcing material may be used solely, or two or more types of carbon-based reinforcing materials may be used as a mixture. For example, two or more types of carbon-based reinforcing materials respectively having different qualities of materials, average particle diameters and forms may be used in combination.

<Silicate-Based Reinforcing Material>

In the present invention, the silicate-based reinforcing material can also be used. As a fibrous filler, wollastonite, etc. can be used, and as a plate-like filler, talc, mica, etc. can be used. One type of a silicate-based reinforcing material may be used solely, or two or more types of silicate-based reinforcing materials may be used as a mixture.

<Other Inorganic Fillers>

As other fibrous fillers, metal fibers and whiskers such as potassium titanate whisker, calcium carbonate whisker, aluminium borate whisker, titanium oxide whisker, zinc oxide whisker and magnesium sulfate whisker can be used. As other plate-like fillers, metal flakes, silica, alumina, calcium carbonate, etc. can be used. Similarly, regarding the above-described other inorganic fillers, one type may be used solely, or two or more types may be used as a mixture.

These fibrous or plate-like inorganic fillers may be subjected to the surface treatment using a surface treatment agent, and by the surface treatment, adhesion between the resin component and the fibrous or plate-like inorganic fillers is improved, thereby realizing high mechanical strength.

[Fluoropolymer (D)]

The polycarbonate resin composition of the present invention contains the fluoropolymer (D) as a dripping prevention agent. Further, as the fluoropolymer, one type of a fluoropolymer may be used, or two or more types of fluoropolymers may be used with any combination and any ratio.

Specific examples of the fluoropolymer include a fluorinated polyolefin such as polyfluoroethylene. The fluorinated polyolefin is a polymer or copolymer containing a fluoroethylene structure. The polymer or copolymer containing a fluoroethylene structure is a polymer mainly composed of a fluoroethylene structure (structural unit). Specifically, the ratio of the fluoroethylene structure (structural unit of fluoroethylene) is preferably 40 to 100% by mass, more preferably 50 to 100% by mass, and even more preferably 60 to 100% by mass of all the monomer units constituting the fluorinated polyolefin.

Specific examples thereof include polydifluoroethylene, a polytetrafluoroethylene resin, a tetrafluoroethylene/hexafluoropropylene copolymer and a tetrafluoroethylene/perfluoroalkylvinylether copolymer. Among them, preferred is a polytetrafluoroethylene resin in terms of flame retardance, and particularly preferred is a polytetrafluoroethylene having fibril-forming ability. This is easily dispersed in polymers and shows a tendency to bond polymers together to produce a fibrous material. The polytetrafluoroethylene having fibril-forming ability is classified into Type 3 according to the ASTM Standard. The polytetrafluoroethylene can be used in a solid form or in an aqueous dispersion form. As the polytetrafluoroethylene having fibril-forming ability, for example, "Teflon (registered trademark) 6J" and "Teflon (registered trademark) 30J" manufactured by Du Pont-Mitsui Fluorochemicals Co., Ltd., and Polyflon (trade name) series (e.g., "Polyflon FA-500H") manufactured by Daikin Industries, Ltd. are commercially available. The number-average molecular weight of the polytetrafluoroethylene is not particularly limited, but it is preferably 3,000,000 to tens of millions (e.g., 3,000,000 to 90,000,000).

[Polycarbonate Resin Composition]

The polycarbonate resin composition of the present invention (100% by mass) contains 18 to 75% by mass of the polycarbonate resin (A) having a viscosity average molecular weight of 28,000 to 60,000, 5 to 30% by mass of the phosphorus-based flame retardant (B), 18 to 50% by mass of the fibrous or plate-like inorganic filler (C) and 0.1 to 2% by mass of the fluoropolymer (D).

When the content of the polycarbonate resin (A) is less than 18% by mass, toughness of the resin composition may be reduced, and when the content is more than 75% by mass, mechanical strength and flame retardance may be insufficient. The content of the polycarbonate resin (A) is preferably 27 to 71% by mass, and more preferably 34 to 68% by mass in terms of toughness, mechanical strength and flame retardance.

The content of the phosphorus-based flame retardant (B) in the polycarbonate resin composition is preferably controlled so that the melt volume rate (MVR) (300° C., 1.2 kg) of the polycarbonate resin composition becomes 2.0 to 10 $cm^3/10$ min. Since the phosphorus-based flame retardant (B), particularly the phosphoric acid ester-based flame retardant generally has flowability improvement effect, there is a tendency that the larger the content of the phosphorus-based flame retardant (B) is, the larger the melt volume rate of the composition is. When the content of the phosphorus-based flame retardant (B) is less than 5% by mass, though dripping at the time of burning is suppressed, the burning time may become longer. Meanwhile, when the adding amount of the phosphorus-based flame retardant (B) is more than 30% by mass, dripping at the time of burning, reduction in heat resistance and reduction in toughness of a matrix resin may occur.

Further, the amount of the phosphorus-based flame retardant (B) to be added is preferably 6 to 25% by mass, more preferably 7 to 20% by mass, and even more preferably 10 to 20% by mass in terms of flame retardance and heat resistance. In particular, in order to achieve a balance between excellent flame retardance and excellent heat resistance, a phosphazene compound is preferably used as the phosphorus-based flame retardant (B) in an adding amount within the above-described range.

The content of the fibrous or plate-like inorganic filler (C) is preferably 22.5 to 50% by mass, more preferably 22.5 to 47.5% by mass, and even more preferably 25 to 45% by mass. When the content is less than the above-described lower limit, the effect of improving strength exerted by blending of a reinforcing filler (B) (in particular, the effect of improving bending characteristics) cannot be sufficiently obtained, and when the content is more than the above-described upper limit, surface smoothness tends to be impaired.

When the content of the fluoropolymer (D) is less than 0.1% by mass, the effect of improving flame retardance exerted by the fluoropolymer may be insufficient. When the content of the fluoropolymer is more than 2% by mass, poor outer appearance and reduction in mechanical strength of molded products obtained by molding the polycarbonate resin composition may occur. The content of the fluoropolymer (D) is preferably 0.1 to 1.0% by mass, and more preferably 0.15 to 0.75% by mass from the viewpoint of further improvement of flame retardance and ensuring of outer appearance and mechanical strength of molded products. When the content of the fluoropolymer is less than the lower limit of the above-described range, the effect of improving flame retardance exerted by the fluoropolymer may be insufficient. When the content of the fluoropolymer is more than the upper limit of the above-described range, poor outer appearance and reduction in mechanical strength of molded products obtained by molding the polycarbonate resin composition may occur.

[Other Components]

(Other Resin Components)

The aromatic polycarbonate resin composition of the present invention may contain resin components other than the polycarbonate resin (A) and the fluoropolymer (D) within a range in which the purpose of the present invention is not impaired. Examples of other resin components which can be blended include a polystyrene resin, a high impact polystyrene resin, a hydrogenated polystyrene resin, a polyacrylstyrene resin, an ABS resin, an AS resin, an AES resin, an ASA resin, an SMA resin, a polyalkyl methacrylate resin, a polymethacrylic methacrylate resin, a polyphenylether resin, a polycarbonate resin other than the component (A), an amorphous polyalkylene terephthalate resin, a polyester resin, an amorphous polyamide resin, poly-4-methylpentene-1, a cyclic polyolefin resin, an amorphous polyarylate resin and polyethersulfone. These components may be used solely, or two or more of them may be used in combination.
(Other Additives)

The aromatic polycarbonate resin composition of the present invention may further contain various additives within a range in which the effects of the present invention are not reduced. Examples of such additives include a thermal stabilizer, an antioxidant, a mold release agent, an ultraviolet absorber, a stain pigment, an antistatic agent, a flame retardant, a dripping prevention agent, an impact strength modifier, a plasticizer, a dispersing agent and an antimicrobial agent. One type of such an additive may be contained, or two or more types of such additives may be contained with any combination and any ratio.

[Method for Producing Polycarbonate Resin Composition]

The method for producing the polycarbonate resin composition of the present invention is not limited, and a wide range of publicly-known methods for producing a polycarbonate resin composition can be employed.

Specific examples thereof include a method in which the polycarbonate resin (A), the phosphorus-based flame retardant (B), the fibrous or plate-like inorganic filler (C) and the fluoropolymer (D) of the present invention, and other components, which are blended according to need, are mixed together in advance using, for example, a mixing machine such as a tumbler, a Henschel mixer and a super mixer, and then the mixture is melt-kneaded using a mixing machine such as a Bunbury mixer, a roller, a Brabender, a single screw kneading extruder, a twin screw kneading extruder and a kneader.

Further, for example, it is also possible to produce the thermoplastic resin composition of the present invention by not mixing components in advance or mixing only a part of components in advance and by carrying out supply to an extruder using a side feeder for melt-kneading. In particular, since the inorganic filler (C) suppresses crushing, it is preferably supplied from a side feeder placed at the downstream side of the extruder, separately from the resin component, to be mixed.

[Flowability of Polycarbonate Resin Composition]

The melt volume rate (MVR) (cm$^3$/10 min) of the polycarbonate resin composition of the present invention, which is measured using a melt indexer in accordance with ISO 1133 under a heating temperature of 300° C., a load of 1.2 kg and a preheating time of 500 seconds, is preferably 2.0 to 10 cm$^3$/10 min. When the melt volume rate is 2.0 cm$^3$/10 min or more, it is possible to prevent reduction in productivity due to increase of torque at the time of melt extrusion of a sheet/film. When the melt volume rate is 10 cm$^3$/10 min or less, it is possible to suppress dripping at the time of burning. The melt volume rate is more preferably 2.0 to 9.0 cm$^3$/10 min, even more preferably 2.0 to 8.0 cm$^3$/10 min, and particularly preferably 2.0 to 6.0 cm$^3$/10 min By adjusting the melt volume rate within the above-described range, dripping at the time of burning can be prevented and a sheet having good flame retardance can be obtained.

[Glass Transition Temperature of Resin Component]

The glass transition temperature of the resin component of the present invention is preferably 75 to 170° C., more preferably 85 to 160° C., and particularly preferably 95 to 150° C. When the glass transition temperature is 75° C. or higher, excellent heat resistance can be obtained, and when the glass transition temperature is 170° C. or lower, good molding processability can be obtained. Note that the resin component as used herein refers to a component including the component (A), the component (B) and the component (D), wherein inorganic fillers such as the component (C) are excluded from the polycarbonate resin composition of the present invention.

[Method for Producing Sheet or Film]

The polycarbonate resin composition of the present invention can be made into molded bodies with various forms. In particular, when using the polycarbonate resin composition of the present invention, it is possible to provide a thin-walled molded product having excellent flame retardance, which is difficult to be realized by conventional polycarbonate resin compositions. Examples of applications of the molded product of the present invention include electrical and electronic equipments, office automation equipments, information terminal devices, machine components, home appliances, vehicle components, building components, various containers, leisure goods/sundries and components for lighting equipments, etc. In particular, because of excellent flame retardance, the molded product of the present invention is suitably used for electrical and electronic equipments, office automation equipments, information terminal devices, home appliances, components for lighting equipments, etc. and nameplates, and particularly suitably used for electrical and electronic equipments, components for lighting equipments and sheet members. In particular, the polycarbonate resin composition of the present invention is suitably used for molding into a sheet or film, and a sheet or film having excellent heat resistance, mechanical strength (particularly rigidity) and thin-wall flame retardance is obtained.

As the method for producing the polycarbonate resin sheet or film of the present invention, the melt extrusion method (e.g., T-die molding method) is suitably used. Specifically, according to one embodiment of the present invention, a method for producing a sheet or film, which includes a step of extrusion molding the polycarbonate resin composition, is provided.

In the present invention, a non-reinforced thermoplastic resin layer may be laminated on one or both of surfaces of the outer layer of the sheet or film made of the polycarbonate resin. Specifically, according to one embodiment of the present invention, a laminated sheet or film, which has a thermoplastic resin layer on at least one surface of the polycarbonate resin layer, is provided. By employing this embodiment, good surface smoothness, glossiness and impact resistance can be obtained, and when printing is made on the back surface of the non-reinforced layer, deep outer appearance can be obtained.

Further, the thermoplastic resin to be laminated may contain various additives. Examples of such additives include a stabilizer, an antioxidant, a mold release agent, an ultraviolet absorber, a stain pigment, an antistatic agent, a flame retardant, an impact strength modifier, a plasticizer, a dispersing agent and an antimicrobial agent. One type of such an additive for resin may be contained, or two or more types of such additives may be contained with any combination and any ratio.

Note that the "sheet" generally refers to a thin and flat product whose thickness is small considering the length and width thereof, and the "film" refers to a thin and flat product whose thickness is extremely small considering the length and width thereof, wherein the maximum thickness is arbitrarily limited, which is usually supplied in the form of a roll. However, in this specification, the "sheet" is not clearly distinguished from the "film", and these terms are used as the same meaning.

[Thickness of Film/Sheet]

The thickness of the film or sheet obtained from the polycarbonate resin composition of the present invention (polycarbonate resin layer in the case of a laminated body) is preferably 400 to 1200 µm, more preferably 400 to 1000 µm, even more preferably 500 to 1000 µm, and still more preferably 500 to 800 µm. When the thickness is adjusted to 400 µm or more, high rigidity can be obtained, and when the thickness is adjusted to 1200 µm or less, the film or sheet can be suitably used for cases of electrical and electronic equipments, etc., which require reduction in the thickness.

[Bending Characteristics of Film/Sheet]

The bending elastic modulus of the film or sheet obtained from the polycarbonate resin composition of the present invention is preferably 5 GPa or more, more preferably 6 GPa or more, and even more preferably 8 GPa or more. The higher the upper limit is, the better, but it is usually 15 GPa or less. In the present invention, the bending elastic modulus of the film or sheet can be measured in a manner in which a molded sheet having a thickness of 0.6 mm is punched to have a dumbbell test piece shape and it is subjected to the bending test in the sheet extrusion direction (flow direction) under a width of 10 mm, a distance of 40 mm between support points and a test speed of 2 mm/min, using Autograph AGS-X manufactured by Shimadzu Corporation.

[Flame Retardance of Film/Sheet]

The film or sheet obtained from the resin composition of the present invention has excellent flame retardance. Specifically, when it is evaluated by a method in accordance with the UL94V test, it is preferably evaluated as V-1 or V-0, and more preferably evaluated as V-0. Note that the UL94V test can be conducted by the method described in the Examples below.

EXAMPLES

Hereinafter, the present invention will be specifically described by way of working examples and comparative examples. However, the present invention is not limited thereby and can be arbitrarily changed and then carried out within a range in which the effects of the present invention are exerted.

Methods for measurement/evaluation used in the working examples and comparative examples are described below.

[Methods for Measurement/Evaluation]

<Pellet Flowability>

The melt volume rate (cm³/10 min) of a resin composition pellet was measured in accordance with ISO 1133 under a heating temperature of 300° C., a load of 1.2 kg, a preheating time of 500 seconds, using G-01 manufactured by Toyo Seiki Seisaku-sho, Ltd.

<Flame Retardance>

A resin sheet was cut into a size having a length of 125 mm and a width of 13 mm, thereby preparing a test piece for the flame retardance test. The test piece was subjected to humidity control in a thermostatic chamber (temperature: 23° C., humidity: 50%) for 48 hours to conduct a burning test in accordance with the UL94V test (burning test for plastic materials for parts of devices) established by Underwriters Laboratories (UL, US). UL94V is a method for evaluating flame retardance based on the lingering flame time and dripping property of a vertically-retained test piece having a predetermined size after it is exposed to a burner flame for 10 seconds. For flame retardance to be evaluated as V-0, V-1 or V-2, the criteria shown in Table 1 below must be satisfied.

TABLE 1

|  | V-0 | V-1 | V-2 |
| --- | --- | --- | --- |
| Maximum lingering flame time of each sample | 10 sec or shorter | 30 sec or shorter | 30 sec or shorter |
| Total lingering flame time of 5 samples | 50 sec or shorter | 250 sec or shorter | 250 sec or shorter |
| Cotton ignition due to dripping | Not ignited | Not ignited | Ignited |

In this regard, the lingering flame time refers to duration of continuous flaming of a test piece after keeping an ignition source away from the test piece. Further, cotton ignition due to dripping is determined by whether or not the cotton as an indicator placed about 300 mm below the lower end of the test piece is ignited by drips from the test piece. When at least one of 5 samples does not satisfy the above-described criteria, this case is regarded as not satisfying V-2 and evaluated as NR (Not Rated).

The results are shown in Tables 2 and 3. Note that the evaluation is described as "UL flame retardance" in the tables.

<Bending Characteristics>

A molded sheet was punched to have a dumbbell test piece shape and it was subjected to the bending test in the sheet extrusion direction (flow direction) under a width of 10 mm, a distance of 40 mm between support points and a test speed of 2 mm/min, using Autograph AGS-X manufactured by Shimadzu Corporation, thereby measuring the bending elastic modulus.

The case where it was less than 5 GPa can be evaluated as "poor", the case where it was 5 GPa or more and less than 8 GPa can be evaluated as "good", and the case where it was 8 GPa or more can be evaluated as "best".

<Heat Resistance>

The glass transition temperature of the resin component was measured by a differential scanning calorimetry SSC-5200 (DSC) manufactured by Seiko Instruments & Electronics Ltd. at a temperature raising rate of 10° C./min. In the measurement, the temperature was elevated to a temperature at which the resin component was melted (260° C.) at a rate of 20° C./min, rapidly cooled to −30° C., and then the temperature was elevated again at a rate of 10° C./min (2nd run). The value obtained by calculation based on the profile of the 2nd run was regarded as the glass transition temperature.

The case where it was lower than 75° C. can be evaluated as "poor", and the case where it was 75° C. or higher can be evaluated as "good".

<Outer Appearance>

The sheet produced by the aforementioned method was visually observed, and the outer appearance thereof was evaluated according to the below-described criteria.

◯: No white spot-like foreign matter or the like was observed, and the sheet had good outer appearance.

x: A white spot-like foreign matter was observed.

Example 1

To 53.42% by mass of polycarbonate powder (viscosity average molecular weight (Mv): 40,000, K-4000F manufactured by Mitsubishi Engineering-Plastics Corporation: polycarbonate produced from bisphenol A and carbonyl chloride by means of the interfacial polymerization method), 0.03% by mass of a phosphorus-based antioxidant (PEP36 manufactured by ADEKA Corporation), 0.05% by mass of a heat stabilizer (AO-60 manufactured by ADEKA Corporation), 15% by mass of a phenoxyphosphazene-based flame retardant ("Rabitle FP-110T" manufactured by Fushimi Pharmaceutical Co., Ltd.; a compound, wherein m>3 (main structure: cyclic trimer) and $R^5$ is a phenyl group in formula (IIIa) above), 0.5% by mass of PTFE (polytetrafluoroethylene having fibril-forming ability; Polyflon FA-500H manufactured by Daikin Industries, Ltd.), and 1.0% by mass of carbon black as a stain pigment for coloring (trade name: "Color Black FW18", manufactured by Evonik Degussa Corporation) were added to be mixed in a tumbler (the same applies to the Examples and Comparative Examples below).

The mixed powder of the polycarbonate and the additives obtained as described above was put into a material feed port (hopper) of a twin screw extruder (TEX30α) to prepare a pellet by means of melt extrusion at 300° C. In this regard, the discharge rate of the twin screw extruder TEX30α was 20 kg/hour, and the screw rotation speed thereof was 200 rpm. As the fibrous or plate-like inorganic filler, a glass fiber ("T-571" manufactured by Nippon Electric Glass Co., Ltd.: glass chopped strand (average fiber diameter: 13 μm, average fiber length: 3 mm, aminosilane treatment, bundling with heat-resistant urethane, cross-section shape: circular)) was supplied from the downstream side of the extruder using a side feeder in a manner such that the amount thereof was adjusted to 30% by mass.

The obtained pellet of the polycarbonate resin composition was molded using an extruder to obtain a molded product of film (sheet). In this regard, extrusion molding conditions were as described below.
Extruder: twin screw extruder manufactured by The Japan Steel Works, Ltd.
Size of molded product: width: 400 mm×thickness: 0.6 mm×length: 10 m
Cylinder temperature: 290° C.
Die temperature: 290° C.
Roll temperature: 110° C.
Discharge rate: 23 kg/h
Roll speed: 1.1 m/min The same extruder and extrusion molding conditions were employed in the Examples and Comparative Examples below.

Example 2

The process was carried out in a manner similar to that in Example 1, except that the viscosity average molecular weight (Mv) of polycarbonate powder was 28,000 (E-2000F manufactured by Mitsubishi Engineering-Plastics Corporation: polycarbonate produced from bisphenol A and carbonyl chloride by means of the interfacial polymerization method).

Example 3

The process was carried out in a manner similar to that in Example 2, except that the flame retardant (Rabitle FP-110T manufactured by Fushimi Pharmaceutical Co., Ltd.) was used in an amount of 5% by mass.

Example 4

The process was carried out in a manner similar to that in Example 1, except that the flame retardant (Rabitle FP-110T manufactured by Fushimi Pharmaceutical Co., Ltd.) was used in an amount of 30% by mass.

Example 5

The process was carried out in a manner similar to that in Example 1, except that 12.5% by mass of a condensed phosphoric acid ester (PX-200 manufactured by Daihachi Chemical Industry Co., Ltd.) was used as the flame retardant.

Example 6

The process was carried out in a manner similar to that in Example 1, except that the glass fiber (T-571 manufactured by Nippon Electric Glass Co., Ltd.) was used in an amount of 20% by mass.

Example 7

The process was carried out in a manner similar to that in Example 1, except that the glass fiber (T-571 manufactured by Nippon Electric Glass Co., Ltd.) was used in an amount of 40% by mass.

Example 8

The process was carried out in a manner similar to that in Example 1, except that the glass fiber (T-571 manufactured by Nippon Electric Glass Co., Ltd.) was used in an amount of 50% by mass.

Example 9

The process was carried out in a manner similar to that in Example 1, except that PTFE (Polyflon FA-500H manufactured by Daikin Industries, Ltd.) was used in an amount of 0.1% by mass.

Example 10

The process was carried out in a manner similar to that in Example 1, except that PTFE (Polyflon FA-500H manufactured by Daikin Industries, Ltd.) was used in an amount of 2.0% by mass.

Example 11

The process was carried out in a manner similar to that in Example 2, except that the flame retardant (Rabitle FP-110T manufactured by Fushimi Pharmaceutical Co., Ltd.) was used in an amount of 10% by mass, PTFE (Polyflon FA-500H manufactured by Daikin Industries, Ltd.) was used in an amount of 0.4% by mass and the thickness of the film molded product (sheet) was 0.8 mm.

Example 12

The process was carried out in a manner similar to that in Example 1, except that 17.5% by mass of a condensed phosphoric acid ester (PX-200 manufactured by Daihachi Chemical Industry Co., Ltd.) was used as the flame retardant.

Comparative Example 1

The process was carried out in a manner similar to that in Example 1, except that the viscosity-average molecular weight (Mv) of the polycarbonate powder was 23,000 (S-3000F manufactured by Mitsubishi Engineering-Plastics Corporation).

Comparative Example 2

The process was carried out in a manner similar to that in Example 1, except that the viscosity-average molecular weight (Mv) of the polycarbonate powder was 80,000 (polycarbonate produced from bisphenol A and carbonyl chloride by means of the interfacial polymerization method).

Comparative Example 3

The process was carried out in a manner similar to that in Example 1, except that the flame retardant (Rabitle FP-110T manufactured by Fushimi Pharmaceutical Co., Ltd.) was used in an amount of 2% by mass.

Comparative Example 4

The process was carried out in a manner similar to that in Example 1, except that the flame retardant (Rabitle FP-110T manufactured by Fushimi Pharmaceutical Co., Ltd.) was used in an amount of 32% by mass.

Comparative Example 5

The process was carried out in a manner similar to that in Example 1, except that the glass fiber (T-571 manufactured by Nippon Electric Glass Co., Ltd.) was used in an amount of 15% by mass.

Comparative Example 6

The process was carried out in a manner similar to that in Example 1, except that the glass fiber (T-571 manufactured by Nippon Electric Glass Co., Ltd.) was used in an amount of 52% by mass.

Comparative Example 7

The process was carried out in a manner similar to that in Example 1, except that PTFE (Polyflon FA-500H manufactured by Daikin Industries, Ltd.) was used in an amount of 0.05% by mass.

Comparative Example 8

The process was carried out in a manner similar to that in Example 1, except that PTFE (Polyflon FA-50011 manufactured by Daikin Industries, Ltd.) was used in an amount of 2.5% by mass.

Comparative Example 9

The process was carried out in a manner similar to that in Example 1, except that glass beads ("EGB731B" manufactured by Potters-Ballotini Co., Ltd., average particle diameter: 18 μm, aminosilane treatment) were used instead of the glass fiber.

Table 2

| | | | | Example 1 | Example 2 | Example 3 | Example 4 | Example 5 | Example 6 |
|---|---|---|---|---|---|---|---|---|---|
| Resin composition % | (A)PC | (a-1) | K-4000F | 53.42 | | | 38.42 | 55.92 | 63.42 |
| | | (a-2) | E-2000F | | 53.42 | 63.42 | | | |
| | | (a-3) | S-3000F | | | | | | |
| | | (a-4) | Mv = 80,000 | | | | | | |
| | (B) phosphorus-based flame retardant | (b-1) | FP-110T | 15 | 15 | 5 | 30 | | 15 |
| | | (b-2) | PX-200 | | | | | 12.5 | |
| | (C) inorganic filler | (c-1) | T-571 | 30 | 30 | 30 | 30 | 30 | 20 |
| | | (c-2) | EGB731B | | | | | | |
| | (D) fluoropolymer | (d) | FA-500H | 0.5 | 0.5 | 0.5 | 0.5 | 0.5 | 0.5 |
| | Others | Carbon black | FW18 | 1.0 | 1.0 | 1.0 | 1.0 | 1.0 | 1.0 |
| | | Antioxidant | PEP-36 | 0.03 | 0.03 | 0.03 | 0.03 | 0.03 | 0.03 |
| | | Heat stabilizer | AO-60 | 0.05 | 0.05 | 0.05 | 0.05 | 0.05 | 0.05 |
| | Total | | | 100 | 100 | 100 | 100 | 100 | 100 |
| | Thickness of sheet | | mm | 0.6 | 0.6 | 0.6 | 0.6 | 0.6 | 0.6 |
| Evaluation | Flowability of pellet | MVR | cm$^3$/10 min | 3.3 | 9.6 | 4.2 | 7.5 | 9.7 | 6.7 |
| | Flame retardance | UL flame retardance | | V-0 | V-0 | V-1 | V-0 | V-1 | V-0 |
| | | Number of times of dripping | | 0 | 4 | 1 | 3 | 5 | 3 |
| | Bending characteristics | Bending elastic modulus | GPa | 8.5 | 8.5 | 8.5 | 8.5 | 8.5 | 5.8 |
| | Heat resistance | Glass transition temperature | °C. | 114 | 114 | 144 | 76 | 109 | 114 |
| | Outer appearance | | | ○ | ○ | ○ | ○ | ○ | ○ |

| | | | | Example 7 | Example 8 | Example 9 | Example 10 | Example 11 | Example 12 |
|---|---|---|---|---|---|---|---|---|---|
| Resin composition % | (A)PC | (a-1) | K-4000F | 43.42 | 30.92 | 53.82 | 51.92 | | 50.92 |
| | | (a-2) | E-2000F | | | | | 58.52 | |
| | | (a-3) | S-3000F | | | | | | |
| | | (a-4) | Mv = 80,000 | | | | | | |
| | (B) phosphorus-based flame retardant | (b-1) | FP-110T | 15 | 17.5 | 15 | 15 | 10 | |
| | | (b-2) | PX-200 | | | | | | 17.5 |
| | (C) inorganic filler | (c-1) | T-571 | 40 | 50 | 30 | 30 | 30 | 30 |

TABLE 2-continued

|  |  |  |  |  |  |  |  |  |  |
|---|---|---|---|---|---|---|---|---|---|
|  | (D) fluoropolymer | (c-2) | EGB731B |  |  |  |  |  |  |
|  |  | (d) | FA-500H | 0.5 | 0.5 | 0.1 | 2 | 0.4 | 0.5 |
|  | Others | Carbon black | FW18 | 1.0 | 1.0 | 1.0 | 1.0 | 1.0 | 1.0 |
|  |  | Antioxidant | PEP-36 | 0.03 | 0.03 | 0.03 | 0.03 | 0.03 | 0.03 |
|  |  | Heat stabilizer | AO-60 | 0.05 | 0.05 | 0.05 | 0.05 | 0.05 | 0.05 |
|  | Total |  |  | 100 | 100 | 100 | 100 | 100 | 100 |
|  | Thickness of sheet |  | mm | 0.6 | 0.6 | 0.6 | 0.6 | 0.8 | 0.6 |
| Evaluation | Flowability of pellet | MVR | cm³/10 min | 3.6 | 3.0 | 3.8 | 2.3 | 5.8 | 4.7 |
|  | Flame retardance |  | UL flame retardance | V-0 | V-0 | V-0 | V-0 | V-0 | V-0 |
|  |  |  | Number of times of dripping | 0 | 0 | 0 | 0 | 0 | 0 |
|  | Bending characteristics | Bending elastic modulus | GPa | 11.2 | 13 | 8.5 | 8.5 | 8.5 | 8.5 |
|  | Heat resistance | Glass transition temperature | °C. | 114 | 108 | 114 | 114 | 126 | 93 |
|  | Outer appearance |  |  | ○ | ○ | ○ | ○ | ○ | ○ |

TABLE 3

|  |  |  |  | Comparative Example 1 | Comparative Example 2 | Comparative Example 3 | Comparative Example 4 | Comparative Example 5 |
|---|---|---|---|---|---|---|---|---|
| Resin composition % | (A) PC | (a-1) | K-4000F |  |  | 66.42 | 36.42 | 65.92 |
|  |  | (a-2) | E-2000F |  |  |  |  |  |
|  |  | (a-3) | S-3000F | 53.42 |  |  |  |  |
|  |  | (a-4) | Mv = 80,000 |  | 53.42 |  |  |  |
|  | (B) phosphorus-based flame retardant | (b-1) | FP-110T | 15 | 15 | 2 | 32 | 15 |
|  |  | (b-2) | PX-200 |  |  |  |  |  |
|  | (C) inorganic filler | (c-1) | T-571 | 30 | 30 | 30 | 30 | 17.5 |
|  |  | (c-2) | EGB731B |  |  |  |  |  |
|  | (D) fluoropolymer | (d) | FA-500H | 0.5 | 0.5 | 0.5 | 0.5 | 0.5 |
|  | Others | Carbon black | FW18 | 1.0 | 1.0 | 1.0 | 1.0 | 1.0 |
|  |  | Antioxidant | PEP-36 | 0.03 | 0.03 | 0.03 | 0.03 | 0.03 |
|  |  | Heat stabilizer | AO-60 | 0.05 | 0.05 | 0.05 | 0.05 | 0.05 |
|  | Total |  |  | 100 | 100 | 100 | 100 | 100 |
|  | Thickness of sheet |  | mm | 0.6 | 0.6 | 0.6 | 0.6 | 0.6 |
| Evaluation | Flowability of pellet | MVR | cm³/10 min | 13.8 | — | Unmeasurable | 7.5 | 7.1 |
|  | Flame retardance |  | UL flame retardance | V-2 | — | NR | V-0 | V-0 |
|  |  |  | Number of times of dripping | 5 | — | 0 | 3 | 3 |
|  | Bending characteristics | Bending elastic modulus | GPa | 8.5 | — | 8.5 | 8.5 | 5.5 |
|  | Heat resistance | Glass transition temperature | °C. | 114 | — | 146 | 71 | 114 |
|  | Outer appearance |  |  | ○ | ○ | ○ | ○ | ○ |

|  |  |  |  | Comparative Example 6 | Comparative Example 7 | Comparative Example 8 | Comparative Example 9 |
|---|---|---|---|---|---|---|---|
| Resin composition % | (A) PC | (a-1) | K-4000F | 31.42 | 53.87 | 51.42 | 53.42 |
|  |  | (a-2) | E-2000F |  |  |  |  |
|  |  | (a-3) | S-3000F |  |  |  |  |
|  |  | (a-4) | Mv = 80,000 |  |  |  |  |
|  | (B) phosphorus-based flame retardant | (b-1) | FP-110T | 15 | 15 | 15 | 15 |
|  |  | (b-2) | PX-200 |  |  |  |  |
|  | (C) inorganic filler | (c-1) | T-571 | 52 | 30 | 30 |  |
|  |  | (c-2) | EGB731B |  |  |  | 30 |
|  | (D) fluoropolymer | (d) | FA-500H | 0.5 | 0.05 | 2.5 | 0.5 |
|  | Others | Carbon black | FW18 | 1.0 | 1.0 | 1.0 | 1.0 |
|  |  | Antioxidant | PEP-36 | 0.03 | 0.03 | 0.03 | 0.03 |
|  |  | Heat stabilizer | AO-60 | 0.05 | 0.05 | 0.05 | 0.05 |
|  | Total |  |  | 100 | 100 | 100 | 100 |
|  | Thickness of sheet |  | mm | 0.6 | 0.6 | 0.6 | 0.6 |
| Evaluation | Flowability of pellet | MVR | cm³/10 min | 1.6 | 4.1 | 2.1 | 4.9 |
|  | Flame retardance |  | UL flame retardance | NR | NR | V-0 | V-0 |
|  |  |  | Number of | 0 | 1 | 0 | 0 |

TABLE 3-continued

| | | times of dripping | | | | |
|---|---|---|---|---|---|---|
| Bending characteristics | Bending elastic modulus | GPa | 13.3 | 8.5 | 8.5 | 2.9 |
| Heat resistance | Glass transition temperature | ° C. | 114 | 114 | 114 | 114 |
| | Outer appearance | | ○ | ○ | x | ○ |

The below-described matters are understood from Tables 2 and 3.

In each of Examples 1-12, the polycarbonate resin having a viscosity average molecular weight of 28,000 to 60,000, the phosphorus-based flame retardant, the fibrous or plate-like inorganic filler and the fluoropolymer were contained at a predetermined blending ratio, the melt volume rate of the resin composition pellet was 2.0 to 10 cm$^3$/10 min, and in this case, excellent mechanical properties (bending elastic modulus of 5.8 GPa or more), good flame retardance even in the case where the thickness of the molded product was 0.8 mm or less, and heat resistance (glass transition temperature of 75° C. or higher) were all obtained.

In addition, it is confirmed that when using a phosphazene compound as the phosphorus-based flame retardant, better heat resistance can be obtained compared to the case where a phosphoric acid ester compound is used.

Meanwhile, in Comparative Example 1 in which the viscosity average molecular weight (Mv) of polycarbonate powder was 23,000, since the melt volume rate exceeded 10 cm$^3$/10 min, dripping and cotton ignition occurred at the time of flame contact, and the result corresponded to V-2 of the UL94 vertical burning test standard.

In Comparative Example 2 in which the viscosity average molecular weight (Mv) of polycarbonate powder was 80,000, since the viscosity of the resin composition was very high, the torque at the time of kneading exceeded the upper limit, and it was impossible to prepare a pellet.

In Comparative Example 3 in which the amount of the flame retardant was 2% by mass, the burning time was long, and the result did not meet the UL94 vertical burning test standard.

In Comparative Example 4 in which the amount of the flame retardant was 32% by mass, the glass transition temperature was low, and heat resistance was insufficient.

In Comparative Example 5 in which the amount of the glass fiber was 15% by mass, the bending elastic modulus was low, and mechanical properties were insufficient.

In Comparative Example 6 in which the amount of the glass fiber was 52% by mass, dripping easily occurred because the specific gravity was high, and the result did not meet the UL94 vertical burning test standard.

In Comparative Example 7 in which the amount of PTFE was 0.05% by mass, it was impossible to obtain the effect of preventing dripping, and flame retardance was insufficient.

In Comparative Example 8 in which the amount of PTFE was 2.5% by mass, a white spot-like foreign matter was observed on the surface of the sheet, and outer appearance was not good.

In Comparative Example 9 in which the inorganic filler was glass beads, since it was not a fibrous inorganic filler, the bending elastic modulus was low, and the rigidity was insufficient.

Thus, it was confirmed that a film/sheet having excellent thin-wall flame retardance, which also has excellent heat resistance, excellent mechanical strength, and excellent flame retardance even in the case where the sheet or film is thin, can be obtained by using the polycarbonate resin composition that contains the polycarbonate resin (A) having a specific viscosity average molecular weight, the phosphorus-based flame retardant (B), the fibrous or plate-like inorganic filler (C) and the fluoropolymer (D) each at a specific ratio.

INDUSTRIAL APPLICABILITY

The sheet or film made of the flame-retardant polycarbonate resin of the present invention has high rigidity and excellent flame retardance, and therefore can be suitably used as a sheet or film for cases of electrical and electronic equipments.

The invention claimed is:

1. A polycarbonate resin composition, which contains 18 to 75% by mass of a polycarbonate resin (A) having a viscosity average molecular weight of 35,000 to 60,000, 5 to 30% by mass of a phosphorus-based flame retardant (B), 18 to 50% by mass of a fibrous or plate-like inorganic filler (C) and 0.1 to 2% by mass of a fluoropolymer (D), which has a melt volume rate of 2.0 to 6.0 cm$^3$/10 min under 300° C. and 1.2 kg.

2. The polycarbonate resin composition according to claim 1, wherein the phosphorus-based flame retardant (B) is a phosphazene compound or a condensed-type phosphoric acid ester.

3. The polycarbonate resin composition according to claim 1, wherein the phosphorus-based flame retardant (B) is a phosphazene compound.

4. The polycarbonate resin composition according to claim 1, wherein the content of the inorganic filler (C) is 22.5 to 50% by mass.

5. The polycarbonate resin composition according to claim 1, wherein the inorganic filler (C) is a glass fiber.

6. A sheet or film, wherein the polycarbonate resin composition according to claim 1 is used.

7. The sheet or film according to claim 6, which has a thickness of 400 to 1200 μm.

8. The sheet or film according to claim 6, wherein the evaluation result of a UL94V test is V-0 or V-1.

9. The sheet or film according to claim 6, wherein a resin component containing the polycarbonate resin (A), the phosphorus-based flame retardant (B) and the fluoropolymer (D) has a glass transition temperature of 75° C. or higher.

10. A method for producing a sheet or film, which comprises extrusion molding the polycarbonate resin composition according to claim 1.

* * * * *